United States Patent
Xu et al.

(10) Patent No.: US 6,780,888 B1
(45) Date of Patent: Aug. 24, 2004

(54) SILICON COMPOUNDS DERIVED FROM ASCORBIC ACID

(75) Inventors: Jinzhu Xu, Paris (FR); Hervé Richard, Villepinte (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/111,537

(22) PCT Filed: Sep. 29, 2000

(86) PCT No.: PCT/FR00/02713

§ 371 (c)(1),
(2), (4) Date: May 24, 2002

(87) PCT Pub. No.: WO01/30784

PCT Pub. Date: May 3, 2001

(30) Foreign Application Priority Data

Oct. 26, 1999 (FR) .............................. 99 13355

(51) Int. Cl.$^7$ ..................... A61K 31/341; C07D 307/26
(52) U.S. Cl. ...................... 514/474; 549/214
(58) Field of Search ........................... 514/474; 549/214

(56) References Cited

U.S. PATENT DOCUMENTS

| | | |
|---|---|---|
| 3,220,972 A | 11/1965 | Lamoreaux |
| 3,697,473 A | 10/1972 | Polmanteer et al. |
| 4,340,709 A | 7/1982 | Jeram et al. |
| 5,726,004 A | 3/1998 | Weber et al. |
| 5,843,411 A | 12/1998 | Hernandez et al. |

FOREIGN PATENT DOCUMENTS

| | | |
|---|---|---|
| EP | 0 766 129 | 4/1997 |
| FR | 2 645 863 | 10/1990 |
| WO | WO 92/17184 | 10/1992 |

OTHER PUBLICATIONS

Michael E. Jung et al., "Total Synthesis of (R)–Glycerol Acetonide and the Antiepileptic and Hypotensive Drug (−)–γ–Amino–β–Hydroxybutyric Acid (GABOB): Use of Vitamin C as a Chiral Starting Material", Journal of the American Chemical Society, vol. 102, No. 18, Aug. 27, 1980, pp. 6304–6311.

English language Derwent Abstract of FR 2 645 863, Oct. 19, 1990.

*Primary Examiner*—Taofiq Solola
(74) *Attorney, Agent, or Firm*—Finnegan, Henderson, Farabow, Garrett & Dunner, L.L.P.

(57) ABSTRACT

The invention concerns novel silicon compounds derived from ascorbic acid consisting of a silicon-containing chain or of silanes, comprising at least a radical A of formula (I) wherein: at least one of the radicals L is a divalent radical for fixing A on the silicon chain. The invention further concerns methods for preparing said compounds, compositions, in particular cosmetic or pharmaceutical, containing them, and their use as antioxidant and/or anti-free radical agent, particularly for treating oxidant stress, for treating the effects of exposure to the sun and for preventing ageing.

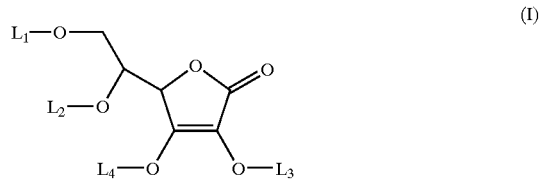

(I)

54 Claims, No Drawings

SILICON COMPOUNDS DERIVED FROM ASCORBIC ACID

This application is a 371 of PCT/FR00/02713 filed Sep. 29, 2000.

The present invention relates to novel fat-soluble and stable silicon-containing derivatives of ascorbic acid. The invention also relates in particular to cosmetic and pharmaceutical compositions comprising these novel derivatives, as well as their use.

A number of derivatives of silicon are known. Thus, patent application FR2645863 describes molecular complexes formed of a compound belonging to the silanol family and of an alkali metal or ammonium derivative of an organic or inorganic acid. Molecular combinations are thus obtained which have the advantage of being soluble in water. This document cites in particular the molecular complex formed of a monomethylsilanetriol and of potassium ascorbate. However, as is specified in this document, the stability of these complexes is not very good, in particular when they are in concentrated solution. In particular, they tend to polymerize, which causes their partial insolubilization. A 2,3,5,6-bis(dimethylsilyl)ascorbate or ascorbosilyl is also known from patent application WO96/10575; in this case, it is a precursor of reactive silanol functions and is therefore also unstable.

The aim of the present invention is to provide novel silicon-containing compounds derived from ascorbic acid, the said compounds being fat-soluble and having good stability both in the dry state and in dilute or concentrated solution.

The subject of the invention is therefore novel silicon-containing compounds derived from ascorbic acid, as are defined below.

Another subject of the invention is a method of preparing the compounds of formulae (2) to (4) defined below, by hydrosilylation of the corresponding siloxane or silane derivative represented by one of the formulae (5) to (7) defined below, on an organic derivative of ascorbic acid chosen from the compounds of formula (I') defined below, followed by deprotection of the compound obtained, for example by acid hydrolysis of the isopropylidenes and/or debenzylation by catalytic hydrogenation.

Another subject of the invention is a method of preparing the silane derivatives of formula (2) defined below by reacting a derivative of formula (I'''), defined below, with a silane derivative of the following formula (8)

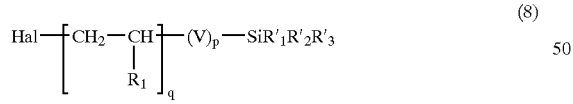
(8)

in which Hal represents a halogen and more particularly chlorine or iodine and the radicals $R_1$, $R'_1$, $R'_2$. $R'_3$, V, p and q have the same meanings as above.

Yet another subject of the invention is an in particular cosmetic or pharmaceutical composition comprising a cosmetically or pharmaceutically acceptable medium and at least one silicon-containing compound derived from ascorbic acid as defined above.

Another subject of the invention is the use of at least one such silicon-containing compound derived from ascorbic acid as antioxidant and/or anti-free-radical agent, in particular in a cosmetic or pharmaceutical composition.

In particular, this use may be cosmetic for, or in a cosmetic composition intended for, treating oxidative stress and/or treating the effects of exposure to sunlight and/or preventing ageing in particular of the skin, the hair, the eyelashes, the eyebrows and/or the nails.

This use may also be for the preparation of a pharmaceutical composition intended for treating oxidative stress and/or treating the effects of exposure to ionizing or solar radiation, and/or preventing ageing in particular of the skin, of the hair, of the eyelashes, of the eyebrows and/or of the nails, and/or treating the effects of the use of certain medicaments which generate free radicals.

Thus, the applicant has found that by covalently grafting one or more ascorbic acid derivatives onto a silicon-containing chain, novel compounds were obtained which had very good properties of solubility in the customary organic solvents, in particular in fatty substances such as oils, as well as high stability in these media or as such.

Moreover, it was observed that these compounds had excellent cosmetic properties.

The compounds according to the invention are therefore characterized in that either they consist of a silicone-containing chain comprising at least one unit of formula (1):

(1)

or they are silanes corresponding to the following formula (2):

in which:

R denotes a linear, cyclic or branched, saturated or unsaturated, optionally partially or completely halogenated, $C_1$–$C_{30}$ hydrocarbon radical or a trimethylsilyloxy group of formula —O—SiMe$_3$;

a is equal to 1 or 2, $R'_1$, $R'_2$, $R'_3$, which are identical or different, are chosen from linear or branched $C_1$–$C_8$ alkyl radicals, linear or branched $C_1$–$C_8$ alkenyl radicals, or a trimethylsilyloxy group;

A is a radical of the following formula (I):

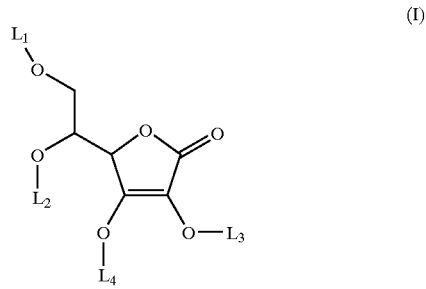
(I)

in which $L_1$, $L_2$, $L_3$ and $L_4$ represent hydrogen or a divalent radical of formula (a) or (a') allowing the attachment of the radical A onto the silicon-containing chain, with the proviso that at least one of the radicals $L_1$, $L_2$, $L_3$ and $L_4$, preferably only one of the said radicals $L_1$, $L_2$, $L_3$ and $L_4$, represents the said divalent radical of the following formula (a) or (a'):

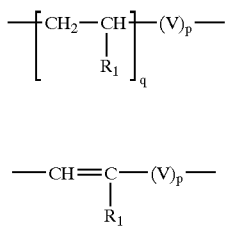

(a)

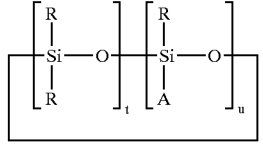

(a')

in which:
V is a linear or branched, saturated or unsaturated, divalent $C_1$–$C_6$ hydrocarbon radical optionally substituted with a hydroxyl radical or a linear or branched, saturated or unsaturated $C_2$–$C_8$ alkoxy radical;
$R_1$ represents a hydrogen atom, a hydroxyl radical or a linear or branched, saturated or unsaturated $C_1$–$C_8$ hydrocarbon radical;
p is 0 or 1, q is 0 or 1, it being understood that p+q is different from 0.

The compounds according to the invention consisting of a silicone-containing chain comprising at least one unit of formula (1) above therefore comprise in particular at least one unit of formula (1a):

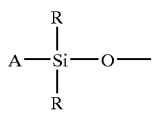

(1a)

and/or at least one unit of formula (1b):

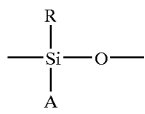

(1b)

Preferably, they may comprise in addition at least one other unit, for example of the (di-)alkylsiloxane type of formula (1c):

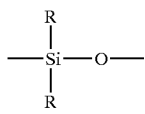

(1c)

Thus, they may in particular be represented by one of the following formulae (3) or (4):

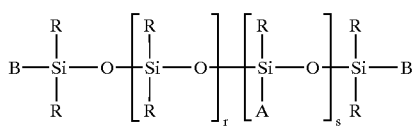

(3)

$$\left[ \begin{array}{c} R \\ | \\ -Si-O- \\ | \\ R \end{array} \right]_t \left[ \begin{array}{c} R \\ | \\ -Si-O- \\ | \\ A \end{array} \right]_u$$ (4)

in which:
the radicals B, which are identical or different, are chosen from the radicals R and A,
r is an integer between 0 and 50 inclusive, preferably between 0 and 5,
s is an integer between 0 and 20 inclusive, preferably chosen from 0, 1 or 2, with the proviso that if s=0, then at least one of the two radicals B represents A,
u is an integer between 1 and 6 inclusive, preferably chosen from 1 or 2,
t is an integer between 0 and 9 inclusive, preferably chosen from 2, 3 or 4,
it being understood that t+u is between 3 and 10 inclusive, and is preferably equal to 3, 4, 5 or 6.

Preferably, the radicals R, which are identical or different, are chosen from linear, cyclic or branched, saturated or unsaturated $C_1$–$C_{18}$ hydrocarbon radicals and linear or branched, saturated or unsaturated, partially halogenated, in particular fluorinated, $C_1$–$C_8$ hydrocarbon radicals.

Still more preferably, the radicals R, which are identical or different, are chosen from linear or branched $C_1$–$C_{10}$ alkyl radicals, the phenyl radical and the linear or branched fluorinated $C_1$–$C_8$ alkyl radicals.

The methyl and 3,3,3-trifluoropropyl radicals may be mentioned in particular. More particularly, at least 80% in numerical terms of the radicals R are methyl radicals.

Preferably, the radicals $R'_1$, $R'_2$, $R'_3$, which are identical or different, are chosen from linear or branched $C_1$–$C_6$ alkyl radicals, in particular methyl or ethyl radicals, and the trimethylsilyloxy group.

In general, the silicon-containing derivatives corresponding to one of the formulae (1), (2), (3) or (4), and having at least one of the following characteristics will be more particularly preferred:
R is $CH_3$;
B is $CH_3$;
$R'_1$, $R'_2$, $R'_3$ represent $CH_3$ or the trimethylsilyloxy group;
$R_1$ is hydrogen or $CH_3$;
V is —$CH_2$— or —$CH_2$—$CH(OH)CH_2$—;
p is 1,
r is between 0 and 5 inclusive,
s is between 1 and 2 inclusive,
t+u is between 3 and 6.

Preferably, the divalent radicals corresponding to the formulae (a) or (a') are chosen from linear or branched, saturated or unsaturated, optionally hydroxylated, divalent $C_1$–$C_6$ hydrocarbon radicals such as the methylene (—$CH_2$—), ethylene (—$CH_2$—$CH_2$—), propylene (—$CH_2$—$CH_2$—$CH_2$—), n-butylene (—$CH_2$—$CH_2$—$CH_2$—$CH_2$—) or isobutylene (—$CH_2$—$CH(CH_3)$—$CH_2$—) radicals, and the radicals —$CH$=$CH$—$CH_2$—, —$CH$=$C$($CH_3$)—$CH_2$—, —$CH$=$CH$—$CH(CH_3)$— and —$CH_2$—$CH(OH)$—$CH_2$—.

Among the preferred silicon-containing derivatives corresponding to the formula (1), and more particularly to the formula (3), the following compounds may be mentioned:
5-(1,2-dihydroxyethyl)-3-hydroxy-4-(3-[1,3,3,3-tetramethyl-1-[(trimethylsilyl)oxy]disiloxanyl]-propyloxy)-5H-furan-2-one, 5-(1,2-dihydroxyethyl)-4-hydroxy-3-(3-[1,3,3,3-tetramethyl-1-[(trimethylsilyl)oxy]disiloxanyl]-propyloxy)-5H-furan-2-one, 5-(1,2-dihydroxyethyl)-3-hydroxy-4-[2-methyl-3-[1,3,3,3-tetramethyl-1-[(trimethylsilyl)oxy]-disiloxanyl]propyloxy]-5H-furan-2-one, 5-(1,2-dihydroxyethyl)-4-hydroxy-3-[2-methyl-3-[1,3,3,3-tetramethyl-1-[(trimethylsilyl)oxy]-disiloxanyl]propyloxy]-5H-furan-2-one, 5-(1,2-dihydroxyethyl)-4-[3-[3-[2-methyl-3-[1,3,3,3-tetramethyl-1-[(trimethylsilyl)oxy]disiloxanyl]-propyloxy]-2-hydroxy-propyloxy]-3-hydroxy-5H-furan-2-one and 5-(1,2-dihydroxyethyl)-3-[3-[3-[2-methyl-3-[1,3,3,3-tetramethyl-1-[(trimethylsilyl)oxy]disiloxanyl]-propyloxy]-2-hydroxy-propyloxy]-4-hydroxy-5H-furan-2-one.

Among the preferred silicon-containing derivatives corresponding to the formula (2), the following compounds may be mentioned:

5-(1,2-dihydroxyethyl)-3-hydroxy-4-trimethylsilanylmethoxy-5H-furan-2-one, 5-(1,2-dihydroxyethyl)-4-hydroxy-3-(3-trimethylsilanylmethoxy)-5H-furan-2-one, 5-(1,2-dihydroxyethyl)-3-hydroxy-4-(3-trimethylsilanylpropyloxy)-5H-furan-2-one, and 5-(1,2-dihydroxyethyl)-4-hydroxy-3-(3-trimethylsilanylpropyloxy)-5H-furan-2-one To prepare the derivatives of formulae (1) to (4), the procedure may be conventionally carried out using a hydrosilylation reaction starting with the corresponding siloxane or silane derivative in which for example all the radicals A are hydrogen atoms. This siloxane or silane derivative is called "SiH-containing derivative" in the remainder of the present description.

The SiH groups may be present in the chain and/or at the ends of the silicon-containing chain. These SiH-containing derivatives are products which are well known in the silicone industry and are generally commercially available. They are for example described in patents U.S. Pat. No. 3,220,972, U.S. Pat. No. 3,697,473 and U.S. Pat. No. 4,340,709.

The SiH-containing derivatives allowing the preparation of the compounds of formulae (2) to (4) may be represented by the following formulae (5) to (7):

$$H\text{—}SiR'_1R'_2R'_3 \tag{5}$$

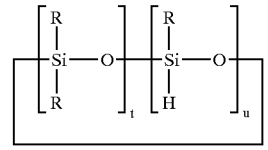

(6)

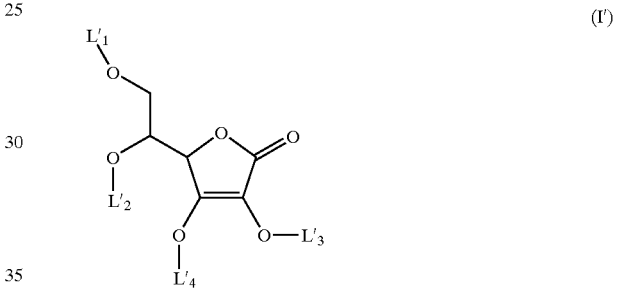

(7)

in which:

R'$_1$, R'$_2$, R'$_3$, R, r, s, t and u have the meaning given above,

B', which are identical or different, are chosen from the radicals R and a hydrogen atom, with the proviso that if s=0, then at least one of the two radicals B' represents H.

To prepare the compounds according to the invention of formulae (2) to (4) above, the procedure may be carried out in the following manner.

A reaction of hydrosilylation of the SiH-containing derivative of formula (5), (6) or (7) is carried out, preferably in the presence of a catalytically effective quantity of a platinum catalyst, on an organic derivative of ascorbic acid chosen from the compounds of the following formula (I'):

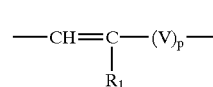

(I')

in which L'$_1$, L'$_2$, L'$_3$ and L'$_4$ represent benzyloxy groups or correspond to one of the following two formulae (b) and (b'):

 (b)

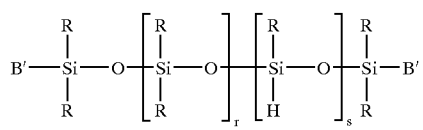

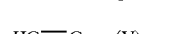 (b')

in which R$_1$, V and p have the same meanings as above, it being possible for the radicals L'$_1$ and L'$_2$ in addition to form together with the ascorbic acid residue a methylenedioxy ring substituted with at least one C$_{1-6}$ alkyl group or a phenyl group, in particular with a methyl, ethyl or phenyl group, or even with two alkyl or phenyl groups;

with the proviso that at least one of the radicals L'$_1$, L'$_2$, L'$_3$ and L'$_4$ represents the radical (b) or (b').

The hydrosilylation reaction can therefore be carried out according to one of the following two reactions:

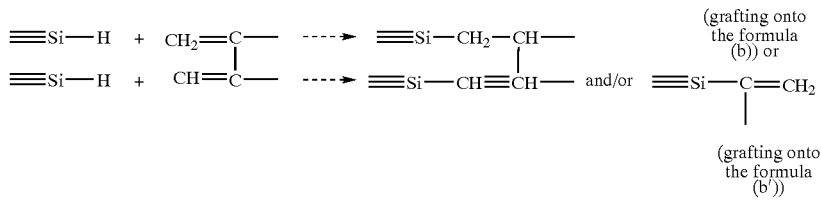

These derivatives (I') may in particular be obtained by condensation, in a conventional manner, of an alkene or alkenyl halide with a derivative of formula (I"):

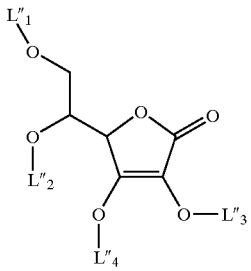
(I")

in which $L''_1$, $L''_2$, $L''_3$ and $L''_4$ represent benzyloxy groups or a hydrogen atom, with the proviso that at least one of the radicals $L''_1$, $L''_2$, $L''_3$ and $L''_4$ represent hydrogen.

These derivatives of formula (I") may be prepared according to the customary procedures which are well known to persons skilled in the art; some are in particular described in patent application EP411184.

After the hydrosilylation of the SiH-containing derivative of formulae (5), (6) or (7) on the ascorbic acid derivative of formula (I'), it is possible to carry out a deprotection of the compound obtained, according to the conventional deprotection methods known in the literature, for example by acid hydrolysis of the isopropylidenes and/or debenzylation by catalytic hydrogenation.

The compounds of formulae (2) to (4) above according to the invention are then obtained.

Moreover, it is possible to prepare the silane derivatives of formula (2) according to another method of synthesis which consists in reacting:

a derivative of formula (I'''):

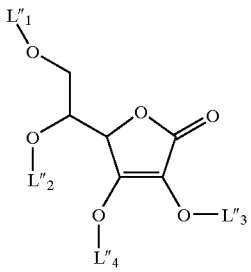
(I''')

in which $L''_1$, $L''_2$, $L''_3$ and $L''_4$ represent benzyloxy groups or a hydrogen atom, it being possible for the radicals $L''_1$, $L''_2$ in addition to form together with the ascorbic acid residue a methylenedioxy ring substituted with at least one $C_{1-6}$ alkyl group or a phenyl group, in particular with a methyl, ethyl or phenyl group, or even with two alkyl or phenyl groups;

with the proviso that at least one of the radicals $L''_1$, $L''_2$, $L''_3$ and $L''_4$ represents hydrogen, with a silane derivative of the following formula (8):

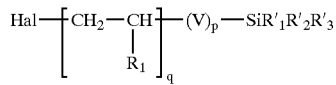
(8)

in which Hal represents a halogen and more particularly chlorine or iodine and the radicals $R_1$, $R'_1$, $R'_2$, $R'_3$, V, p and q have the same meanings as above.

The compounds according to the invention are generally present in the compositions of the invention in proportions of between 0.1% and 10% by weight, preferably between 0.5% and 5% by weight, relative to the total weight of the composition.

These compositions, which may in particular be cosmetic or pharmaceutical compositions, therefore comprise moreover a cosmetically or pharmaceutically acceptable medium, that is to say a medium compatible with all keratinous materials such as the skin of the body or of the face, the mucous membranes, the semi-mucous membranes, the scalp as well as the superficial body growths such as the nails, the hair, the eyelashes and the eyebrows.

The compositions according to the invention may be provided in any cosmetically or pharmaceutically acceptable galenic form, such as in the form of a lotion, suspension, dispersion or solution in solvent or aqueous-alcoholic medium, optionally with a multiphase, optionally thickened or even gelled; in the form of a gel, a foam, a spray or an oil-in-water, water-in-oil or multiple emulsion; in the form of a loose, compact or cast powder; or in the form of a solid or an anhydrous paste.

Persons skilled in the art will be able to choose the appropriate galenic form, as well as its method of preparation, based on their general knowledge, taking into account, on the one hand, the nature of the constituents used, in particular their solubility in the carrier, and, on the other hand, the application envisaged for the composition.

Thus, the composition may comprise at least one ingredient chosen from the adjuvants normally used in the field considered, such as fatty substances, organic solvents, water, silicones, thickeners, emollients, sunscreens, antifoams, moisturizing agents, perfumes, preservatives, surfactants, fillers, sequestrants, anionic, cationic, nonionic and/or amphoteric polymers, propellants, alkalinizing or acidifying agents, colorants, pigments or nanopigments, cosmetic active agents.

Among the fatty substances, there may be mentioned oils and/or waxes, in particular of animal, plant, mineral or synthetic origin; $C_8$–$C_{32}$ fatty acids; $C_8$–$C_{32}$ fatty acid esters; $C_8$–$C_{32}$ fatty alcohols. There may be mentioned more particularly petroleum jelly, paraffin, lanolin, hydrogenated lanolin, acetylated lanolin, hydrogenated palm oil, hydrogenated castor oil, liquid paraffin, paraffin oil, Purcellin oil, silicone oils, volatile or otherwise, isoparaffins.

Among the organic solvents, there may be mentioned $C_1$–$C_6$ lower polyols such as ethanol, isopropanol, propylene glycol, glycerin or sorbitol.

Of course, persons skilled in the art will be careful to choose the possible additional compound(s) cited above and/or their quantities such that the advantageous properties intrinsically attached to the compound in accordance with the invention are not, or not substantially, impaired by the addition(s) envisaged.

It has been observed that the compounds of the invention have an excellent fat-solubility, in particular in fatty substances such as Miglyol, alcohols (in particular ethanol), glycols (in particular propylene glycol) and silicone oils (in particular PDMS). Moreover, they become uniformly distributed in conventional cosmetic carriers containing at least one fatty phase or a cosmetically acceptable organic solvent.

Moreover, it has been observed that the compounds according to the invention could exhibit good antioxidant and/or anti-free-radical properties.

They therefore find a very special application in cosmetic or pharmaceutical compositions intended for treating oxidative stress and/or treating the effects of exposure to sunlight and/or preventing ageing in particular of the skin, of the hair, of the eyelashes, of the eyebrows and/or of the nails.

The compositions comprising them therefore find a very special application as a composition to be applied to the skin of the body and/or of the face, and/or to the hair, eyelashes, eyebrows and/or nails.

In particular, these compositions may be present to be used:

- as a composition for protecting the human epidermis or the hair against UV radiation (antisun compositions);
- as a cosmetic composition for the protection or treatment or care of the hair, in particular in the form of a shampoo, lotion, gel or rinse-off composition, to be applied before or after shampooing, before or after dyeing or bleaching, before, during or after permanent-waving or hair straightening, of a hair-styling or treatment lotion or gel, of a blow-drying or hair-setting lotion or gel, of a hair lacquer, of a composition for permanent-waving or hair straightening, for dyeing or bleaching the hair;
- as a care composition for the skin of the body and/or of the face, such as a treatment cream for the epidermis, day cream, night cream, antiwrinkle cream, moisturizing cream, cream for the hands or the feet;
- as a makeup composition for the eyelashes, the eyebrows, the hair, the body or the face, such as foundation, lipstick, eyeshadow, blusher, eyeliner, mascara, dyeing gel, nail varnish.

The invention is illustrated in greater detail in the following examples.

EXAMPLE 1

Preparation of 5-(1,2-dihydroxyethyl)-3-hydroxy-4-trimethylsilanylmethoxy-5H-furan-2-one

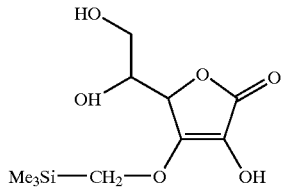

a) 1st step: preparation of 5-(2,2-dimethyl-[1,3]-dioxolan-4-yl)-3-hydroxy-4-trimethylsilanylmethoxy-5H-furan-2-one 19.26 g (0.09 mol) of (iodomethyl)trimethylsilane are added, under nitrogen, to a mixture of 12.96 g (0.06 mol) of 5-(2,2-dimethyl-[1,3]dioxolan-4-yl)-3,4-dihydroxy-5H-furan-2-one (prepared according to M. E. Jung et al. J. Am. Chem. Soc., 1980, 102, 6304) and 7.56 g (0.09 mol) of sodium bicarbonate in 75 ml of dimethyl sulphoxide (DMSO).

The whole is heated at 55° C. for 19 hours. The mixture is cooled and poured into 150 ml of water. The mixture is stirred for 1 hour at room temperature (25° C.). The precipitate is filtered. It is rinsed with water and dried under vacuum.

11.1 g (yield 61%) of the desired product are obtained in the form of a white solid.

$^1$H NMR spectrum (CDCl$_3$, 200 MHz): 4.40 (d, J=4 Hz, 1H); 4.15 (m, 2H); 4.07 (m, 1H); 3.89 (m, 2H); 1.28 (s, 3H); 1.25 (s, 3H); 0.00 (s, 9H).

b) 2nd step: preparation of 5-(1,2-dihydroxyethyl)-3-hydroxy-4-trimethylsilanylmethoxy-5H-furan-2-one The preceding derivative (6.4 g, 0.021 mol) in a mixture of 80 ml of methanol and 40 ml of 2 N aqueous HCl is heated for 2 hours at 50° C. The mixture is evaporated under vacuum at 40° C. in order to remove most of the methanol. The residue is poured into 200 ml of water. The mixture is neutralized with sodium bicarbonate. The mixture is extracted with ethyl acetate. The organic phase is washed with salt water and it is dried over Na$_2$SO$_4$. The solvent is evaporated.

A colourless oil is obtained which is purified on silica (eluant: cyclohexane/ethyl acetate 50/50). 4.0 g (yield 72%) of the desired product are obtained in the form of a colourless oil.

$^1$H NMR spectrum (CDCl$_3$, 200 MHz): 4.54 (d, J=2 Hz, 1H); 4.22 (m, 2H); 3.80 (m, 3H); 0.01 (s, 9H).

EXAMPLE 2

Preparation of 5-(1,2-dihydroxyethyl)-4-hydroxy-3-(3-trimethylsilanylmethoxy)-5H-furan-2-one

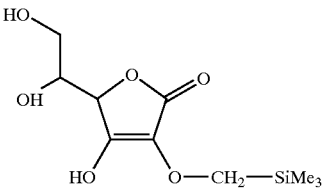

a) 1st step: preparation of 4-benzyloxy-5-(2,2-dimethyl-[1,3]-dioxolan-4-yl)-3-hydroxy-5H-furan-2-one Benzyl bromide (13.0 ml, 0.11 mol) is added to a mixture of 5-(2,2-dimethyl-[1,3]dioxolan-4-yl)-3,4-dihydroxy-5H-furan-2-one (21.62 g, 0.1 mol) and sodium bicarbonate (12.6 g, 0.15 mol) in 125 ml of DMSO, under nitrogen. The mixture is heated at 55° C. for 16 hours. It is cooled and it is poured into 250 ml of water. The mixture is extracted with ethyl acetate. The organic phase is washed with salt water and dried over Na$_2$SO$_4$. The solvent is evaporated.

A brown oil is obtained which is purified on silica (eluant: cyclohexane/ethyl acetate 75/25) to give 13.8 g (yield 45%) of the desired product in the form of a slightly yellow oil.

$^1$H NMR spectrum (CDCl$_3$, 200 MHz): 7.56 (m, 5H); 5.77 (s, 2H); 4.77 (d, J=4 Hz, 1H) 4.46 (m, 1H); 4.20 (m, 2H); 1.55 (s, 3H); 1.48 (s, 3H).

b) 2nd step: preparation of 4-benzyloxy-5-(2,2-dimethyl-[1,3]dioxolan-4-yl)-3-trimethylsilanylmethoxy-5H-furan-2-one (Iodomethyl)trimethylsilane (6.15 g, 0.029 mol) is added to a mixture of the preceding product (8.0 g, 0.026 mol) and potassium carbonate (4.32 g, 0.031 mol) under nitrogen. The mixture is stirred at room temperature for 48 hours. It is poured into 200 ml of water. The mixture is extracted with ethyl acetate. The organic phase is washed with salt water and dried over Na$_2$SO$_4$.

After evaporation of the solvent, an orange-coloured oil (10.5 g) is obtained which is used directly in the next step.

$^1$H NMR spectrum (CDCl$_3$, 200 MHz): 7.27 (m, 5H); 5.34 (s, 2H); 4.40 (d, J=3 Hz, 1H); 4.15 (m, 1H); 3.99 (m, 2H); 3.77 (m, 2H); 1.28 (s, 3H); 1.24 (s, 3H); 0.00 (s, 9H).

c) 3rd step: preparation of 4-benzyloxy-5-(1,2-dihydroxyethyl)-3-trimethylsilanylmethoxy-5H-furan-2-one The preceding product (10.5 g, 0.026 mol) is dissolved in 100 ml of methanol. 50 ml of a 2 N aqueous HCl solution are added. The mixture is heated at 50° C. for 2 hours. The mixture is evaporated under vacuum at 40° C. in order to remove the methanol. The residue is poured into 200 ml of water. The mixture is neutralized with sodium bicarbonate. The mixture is extracted with ethyl acetate. The organic phase is washed with salt water and dried over Na$_2$SO$_4$. The solvent is evaporated to give a yellow oil which is purified on silica (eluant: cyclohexane/ethyl acetate 60/40).

5.6 g (yield 61% in two steps) of the desired product are obtained in the form of a yellowish oil.

$^1$H NMR spectrum (CDCl$_3$, 200 MHz): 7.27 (m, 5H); 5.35 (s, 2H); 4.55 (d, J=3 Hz, 1H); 3.74 (m, 5H); 2.31 (broad d, 1H); 2.06 (t, broad, 1H); 0.00 (s, 9H).

d) 4th step: preparation of 5-(1,2-dihydroxyethyl)-4-hydroxy-3-trimethylsilanylmethoxy-5H-furan-2-one The preceding derivative (5.2 g, 0.015 mol) is dissolved in 100 ml of ethyl acetate. 100 ml of absolute ethanol are added. 1 g of 5% palladium on carbon is then added. The mixture is stirred under 12 bar of hydrogen for 7 hours at room temperature. The catalyst is filtered.

The solvent is evaporated to give 3.8 g (yield 98%) of the desired product in the form of a white solid.

$^1$H NMR spectrum (acetone-d$_6$, 200 MHz): 4.74 (d, J=2 Hz, 1H); 3.82 (m, 1H); 3.71 (m, 2H); 3.63 (m, 2H); 0.00 (s, 9H).

EXAMPLE 3

Preparation of 5-(1,2-dihydroxyethyl)-3-hydroxy-4-(3-trimethylsilanylpropyloxy)-5H-furan-2-one

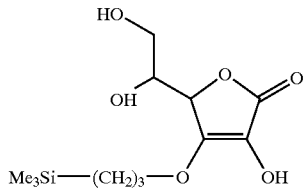

a) 1st step: preparation of 5-(2,2-dimethyl-[1,3]dioxolan-4-yl)-3-hydroxy-4-(3-trimethylsilanylpropyloxy)-5H-furan-2-one 3-iodopropyltrimethylsilane (14.5 g, 0.06 mol) is added to a mixture of 5-(2,2-dimethyl-[1,3]dioxolan-4-yl)-3,4-dihydroxy-5H-furan-2-one (8.64 g, 0.04 mol) and sodium bicarbonate (5.04 g, 0.06 mol) in 50 ml of dimethyl sulphoxide under nitrogen. The mixture is heated at 55° C. for 24 hours. It is cooled and it is poured into 300 ml of water. The mixture is extracted with ethyl acetate. The organic phase is washed with salt water and it is dried over Na$_2$SO$_4$. The solvent is evaporated.

A brown oil is obtained which is purified on silica (eluant: cyclohexane/ethyl acetate 75/25) to give 8.8 g (yield 67%) of the desired product in the form of a slightly yellow oil.

$^1$H NMR spectrum (CDCl$_3$, 200 MHz): 4.53 (d, J=4 Hz, 1H); 4.40 (t, J=7 Hz, 2H); 4.25 (m, 1H); 3.98 (m, 2H); 0.52 (m, 2H); 0.00 (s, 9H).

b) 2nd step: preparation of 5-(1,2-dihydroxyethyl)-3-hydroxy-4-(3-trimethylsilanylpropyloxy)-5H-furan-2-one The preceding product (8.89 g, 0.03 mol) is dissolved in 100 ml of methanol. 50 ml of a 2 N aqueous HCl solution are added. The mixture is heated at 50° C. for 2 hours. The mixture is evaporated under vacuum at 40° C. in order to remove the methanol. The residue is poured into 100 ml of water. The mixture is neutralized with sodium bicarbonate. The mixture is extracted with ethyl acetate. The organic phase is washed with salt water and dried over Na$_2$SO$_4$. The solvent is evaporated. The yellowish oil obtained is purified on silica (eluant: cyclohexane/ethyl acetate 50/50).

5.4 g (yield 62%) of the desired product are obtained in the form of a colourless oil.

$^1$H NMR spectrum (CDCl$_3$, 200 MHz): 4.65 (d, J=2 Hz, 1H); 4.33 (m, 2H); 3.98 (m, 2H); 3.81 (m, 2H); 1.63 (m, 2H); 0.51 (m, 2H); 0.00 (s, 9H).

EXAMPLE 4

Preparation of 5-(1,2-dihydroxyethyl)-4-hydroxy-3-(3-trimethylsilanylpropyloxy)-5H-furan-2-one

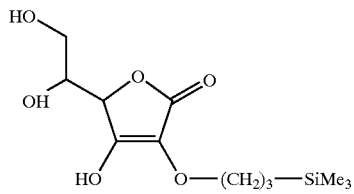

a) 1st step: preparation of 4-benzyloxy-5-(2,2-dimethyl[1,3]dioxolan-4-yl)-3-(3-trimethylsilanylpropyloxy)-5H-furan-2-one 3-iodopropyltrimethylsilane (12.86 g, 0.053 mol) is added to a mixture of 4-benzyloxy-5-(2,2-dimethyl[1,3]dioxolan-4-yl)-3-hydroxy-5H-furan-2-one (14.8 g, 0.048 mol) and potassium carbonate (8.0 g, 0.058 mol), under nitrogen, in 100 ml of dimethyl sulphoxide. The mixture is stirred at room temperature for 22 hours. It is poured into 300 ml of water. The mixture is extracted with ethyl acetate. The organic phase is washed with salt water and dried over Na$_2$SO$_4$.

After evaporation of the solvent, an orange-coloured oil is obtained which is purified on silica (eluant: cyclohexane/ethyl acetate 5/1) to give 10.5 g (yield 52%) of the desired product in the form of a colourless oil.

$^1$H NMR spectrum (CDCl$_3$, 200 MHz): 7.39 (m, 5H); 5.50 (s, 2H); 4.55 (d, J=3 Hz, 1H); 4.30 (m, 1H); 4.01 (m, 4H); 1.67 (m, 2H); 1.40 (s, 3H); 1.37 (s, 3H), 0.50 (m, 2H); 0.00 (s, 9H).

b) 2nd step: preparation of 4-benzyloxy-5-(1,2-dihydroxyethyl)-3-(3-trimethylsilanylpropyloxy)-5H-furan-2-one The preceding product (9.4 g, 0.025 mol) is dissolved in 80 ml of methanol. 40 ml of a 2 N aqueous HCl solution are added. The mixture is heated at 50° C. for 2 hours. The mixture is evaporated under vacuum at 40° C. in order to remove the methanol. The residue is poured into 200 ml of water. The mixture is neutralized with sodium bicarbonate. The mixture is extracted with ethyl acetate. The organic phase is washed with salt water and it is dried over Na$_2$SO$_4$. The solvent is evaporated to give a yellow oil which is purified on silica (eluant: cyclohexane/ethyl acetate 2/1).

8.0 g (yield 94%) of the desired product are obtained in the form of a yellowish oil.

$^1$H NMR spectrum (CDCl$_3$, 200 MHz): 7.39 (m, 5H); 5.50 (s, 2H), 4.71 (d, J=3 Hz, 1H); 4.01 (m, 3H); 3.80 (m, 2H); 2.47 (broad d, 1H); 2.21 (broad t, 1H); 0.50 (m, 2H); 0.00 (s, 9H).

c) 3rd step: preparation of 5-(1,2-dihydroxyethyl)-4-hydroxy-3-(3-trimethylsilanylpropyloxy)-5H-furan-2-one The preceding derivative (7.6 g, 0.02 mol) is dissolved in 100 ml of ethyl acetate. 100 ml of absolute ethanol are added. 1.2 g of 5% palladium on carbon are then added. The mixture is stirred under 12 bar of hydrogen for 7 hours at room temperature. The catalyst is filtered.

The solvent is evaporated and 5.7 g (yield 98%) of the desired product are obtained in the form of a white solid.

$^1$H NMR spectrum (acetone-$d_6$, 200 MHz): 4.84 (d, J=2 Hz, 1H); 3.96 (m, 3H); 3.89 (m, 2H); 1.65 (m, 2H); 0.54 (m, 2H); 0.00 (s, 9H).

EXAMPLE 5

Antisun Cream

An antisun oil-in-water emulsion is prepared comprising:

| | |
|---|---|
| compound of Example 1 | 1 g |
| UV screen (Mexoryl ® XL) | 4 g |
| mixture of cetylstearyl alcohol and oxyethylenated cetylstearyl alcohol (33 EO) 80/20 (DEHSCONET 390 from TENSIA) | 7 g |
| mixture of glyceryl mono- and distearate (CERASYNTH SD from ISP) | 2 g |
| polydimethylsiloxane (DC200 Fluid from DOW CORNING) | 1.5 g |
| benzoate of $C_{12}$–$C_{15}$ alcohols (FINSOLV TN from FINETEX) | 16 g |
| glycerin | 20 g |
| demineralized water | qs 100 g |

EXAMPLE 6

After-shampoo Conditioning Gel for Protecting the Hair

An after-shampoo conditioning gel for protecting the hair is prepared comprising:

| | |
|---|---|
| compound of Example 4 | 2 g |
| polydimethylsiloxane α, Ω-dihydroxylated/volatile silicone (Q2-1401 from DOW CORNING) | 20 g |
| acrylamide/2-acrylamido-2-methylpropanesulphonic acid crosslinked copolymer (SEPIGEL 305 by SEPPIC) | 1 g AM |
| water | qs 100 g |

What is claimed is:

1. A silicon-containing compound derived from ascorbic acid and having at least one group chosen from:

a) silicone-containing chains having at least one group of formula (1):

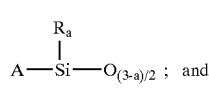
(1)

and b) silanes of formula (2):

$$A\text{—}SiR'_1R'_2R'_3 \quad (2)$$

wherein:

R is chosen from a trimethylsilyloxy group of formula —O—SiMe$_3$, and linear, cyclic and branched, saturated and unsaturated, ($C_1$–$C_{30}$) alkyl groups, wherein the ($C_1$–$C_{30}$) alkyl groups are optionally partially halogenated or optionally completely halogenated;

a is equal to 1 or 2;

R'$_1$, R'$_2$, and R'$_3$, which are identical or different, are each chosen from linear and branched ($C_1$–$C_8$) alkyl groups, linear and branched ($C_1$–$C_8$) alkenyl groups, and trimethylsilyloxy groups of formula —O—SiMe$_3$;

A is chosen from groups of formula (I):

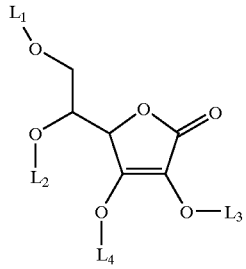
(I)

wherein:

$L_1$, $L_2$, $L_3$, and $L_4$, which are identical or different, are each chosen from hydrogen, divalent groups of formula (a), and divalent groups of formula (a'):

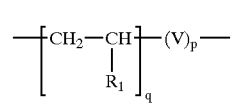
(a)

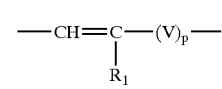
(a')

wherein:

groups V, which are identical or different, are each chosen from linear and branched, saturated and unsaturated, divalent ($C_1$–$C_6$) alkyl groups, wherein said divalent ($C_1$–$C_6$) alkyl groups are optionally substituted with at least one group chosen from linear and branched, saturated and unsaturated ($C_2$–$C_8$) alkoxy groups and hydroxyl groups;

groups $R_1$, which are identical or different, are each chosen from hydrogen, hydroxyl groups, and linear and branched, saturated and unsaturated ($C_1$–$C_8$) alkyl groups; and p is 0 or 1;

q is 0 or 1, with the proviso that that p+q is different from 0;

wherein said divalent groups of formula (a) and divalent groups of formula (a') allow the attachment of the radical A onto the silicon-containing chains; and provided that at least one of $L_1$, $L_2$, $L_3$, and $L_4$ is chosen from said divalent groups of formula (a) and divalent groups of formula (a').

2. A compound according to claim 1, wherein only one of $L_1$, $L_2$, $L_3$, and $L_4$ is chosen from said divalent groups of formula (a) and divalent groups of formula (a').

3. A compound according to claim 1, wherein said silicone-containing chains comprise at least one unit chosen from:

a) units of formula (1a):

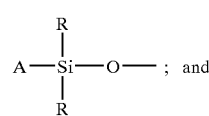
(1a)

and b) units of formula (1b):

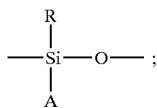
(1b)

wherein:
the groups R, which are identical or different, are each chosen from trimethylsilyloxy groups of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated; and
the groups A, which are identical or different, are each chosen from groups of formula (I):

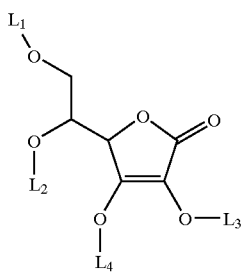
(I)

wherein:
L$_1$, L$_2$, L$_3$, and L$_4$, which are identical or different, are each chosen from hydrogen, divalent groups of formula (a), and divalent groups of formula (a'):

$$-\!\!\left[\text{CH}_2-\underset{R_1}{\text{CH}}\right]_q\!\!-(V)_p-$$
(a)

$$-\text{CH}=\underset{R_1}{C}-(V)_p-$$
(a')

wherein:
the groups V, which are identical or different, are each chosen from linear and branched, saturated and unsaturated, divalent (C$_1$–C$_6$) alkyl groups, wherein said divalent (C$_1$–C$_6$) alkyl groups are optionally substituted with at least one group chosen from linear and branched, saturated and unsaturated (C$_2$–C$_8$) alkoxy groups and hydroxyl groups;
the groups R$_1$, which are identical or different, are each chosen from hydrogen, hydroxyl groups, and linear and branched, saturated and unsaturated (C$_1$–C$_8$) alkyl groups; and
p is 0 or 1;
q is 0 or 1, with the proviso that p+q is different from 0;
wherein said divalent groups of formula (a) and divalent groups of formula (a') allow the attachment of the radical A onto the silicon-containing chain; and
provided that at least one of L$_1$, L$_2$, L$_3$, and L$_4$ is chosen from said divalent groups of formula (a) and divalent groups of formula (a').

4. A compound according to claim 3, wherein said silicone-containing chains further comprise at least one unit chosen from (di-) alkylsiloxane units of formula (1c):

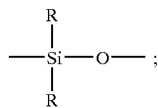
(1c)

wherein:
groups R, which are identical or different, are each chosen from trimethylsilyloxy groups of formula —O—SiMe$_3$ and linear, cyclic and branched, saturated and unsaturated, (C$_1$–C$_{30}$) alkyl groups, wherein the (C$_1$–C$_{30}$) alkyl groups are optionally partially halogenated or optionally completely halogenated.

5. A compound according to claim 4, wherein said compound is chosen from compounds of formula (3) and compounds of formula (4):

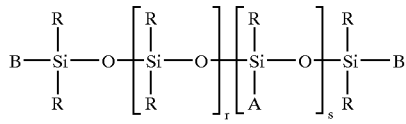
(3)

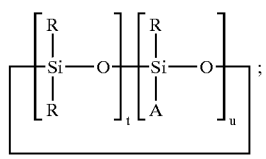
(4)

wherein:
the groups R, which are identical or different, are each chosen from trimethylsilyloxy groups of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated; and
A is chosen from groups of formula (I):

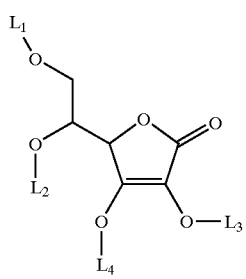
(I)

wherein:
L$_1$, L$_2$, L$_3$, and L$_4$, which are identical or different, are each chosen from hydrogen, divalent groups of formula (a), and divalent groups of formula (a'):

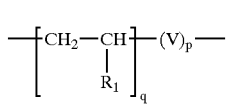
(a)

-continued

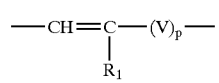

wherein:
groups V, which are identical or different, are chosen from linear and branched, saturated and unsaturated, divalent ($C_1$–$C_6$) alkyl groups, wherein said divalent ($C_1$–$C_6$) alkyl groups are optionally substituted with at least one group chosen from linear and branched, saturated and unsaturated ($C_2$–$C_8$) alkoxy groups and a hydroxyl group;
groups $R_1$, which are identical or different, are chosen from hydrogen, a hydroxyl group, and linear and branched, saturated and unsaturated ($C_1$–$C_8$) alkyl groups; and
p is 0 or 1;
q is 0 or 1, with the proviso that p+q is different from 0; wherein said divalent groups of formula (a) and divalent groups of formula (a') allow the attachment of the radical A onto the silicon-containing chain; and
provided that at least one of $L_1$, $L_2$, $L_3$, and $L_4$ is chosen from said divalent groups of formula (a) and divalent groups of formula (a');
groups B, which are identical or different, are chosen from R and A as defined above;
r ranges from 0 to 50;
s ranges from 0 to 20, provided that if s=0, then at least one of the groups B represents A;
u ranges from 0 to 6;
t ranges from 0 to 9;
with the proviso that t+u ranges from 3 to 10.

6. A compound according to claim 5, wherein r ranges from 0 to 5.

7. A compound according to claim 5, wherein s ranges from 0 to 2.

8. A compound according to claim 5, wherein u is chosen from 1 and 2.

9. A compound according to claim 5, wherein t ranges from 2 to 4.

10. A compound according to claim 5, wherein t+u is chosen from 3, 4, 5, and 6.

11. A compound according to claim 1, wherein the group R is chosen from linear, cyclic, and branched, saturated and unsaturated ($C_1$–$C_{18}$) alkyl groups and partially halogenated, linear and branched, saturated and unsaturated ($C_1$–$C_8$) alkyl group groups.

12. A compound according to claim 11, wherein the group R is chosen from partially fluorinated, linear and branched, saturated and unsaturated ($C_1$–$C_8$) alkyl groups.

13. A compound according to claim 11, wherein the group R is chosen from linear and branched ($C_1$–$C_{10}$) alkyl groups, phenyl groups, and linear and branched, fluorinated ($C_1$–$C_8$) alkyl groups.

14. A compound according to claim 11, wherein the group R is chosen from a methyl group and a 3,3,3-trifluoropropyl group.

15. A compound according to claim 5, wherein at least 80% of the groups R are methyl groups.

16. A compound according to claim 1, wherein $R'_1$, $R'_2$, $R'_3$, which are identical or different, are chosen from linear and branched ($C_1$–$C_6$) alkyl groups and trimethylsilyloxy groups.

17. A compound according to claim 16, wherein $R'_1$, $R'_2$, $R'_3$ are chosen from methyl groups and ethyl groups.

18. A silicon-containing compound derived from ascorbic acid having at least one group chosen from:
a) silicone-containing chains having at least one group of formula (1):

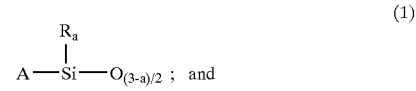

b) silanes of formula (2):

wherein:
R is a methyl group;
a is equal to 1 or 2,
$R'_1$, $R'_2$, and $R'_3$, which are identical or different, are each chosen from methyl groups and trimethylsilyloxy groups of formula —O—SiMe$_3$;
A is chosen from groups of formula (I):

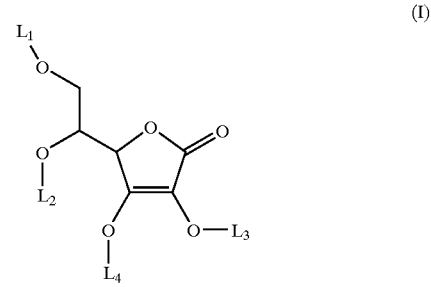

wherein:
$L_1$, $L_2$, $L_3$, and $L_4$, which are identical or different, are each chosen from hydrogen, divalent groups of formula (a), and divalent groups of formula (a'):

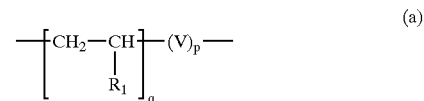

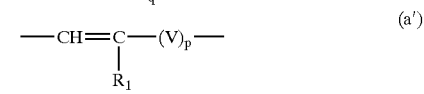

wherein:
groups V which are identical or different, are each chosen from —CH$_2$— groups and —CH$_2$—CH(OH)CH$_2$— groups;
groups $R_1$, which are identical or different, are each chosen from hydrogen and methyl groups; and
p is 0 or 1;
q is 0 or 1, with the proviso that p+q is different from 0;
wherein said divalent groups of formula (a) and divalent groups of formula (a') allow the attachment of the group A onto the silicon-containing chains; and
provided that at least one of $L_1$, $L_2$, $L_3$, and $L_4$ is chosen from said divalent groups of formula (a) and divalent groups of formula (a').

19. A compound chosen from compounds of formula (3) and compounds of formula (4):

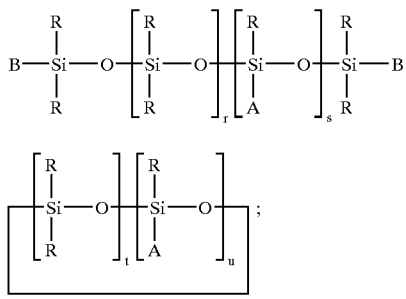

(3)

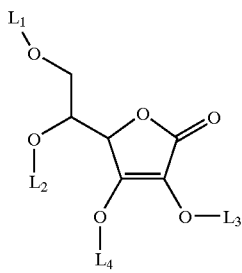

(4)

wherein:
groups R are methyl groups;
groups A, which are identical or different, are chosen from groups of formula (I):

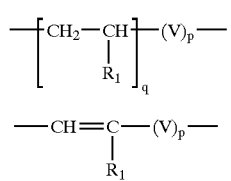

(I)

wherein:
$L_1$, $L_2$, $L_3$, and $L_4$, which are identical or different, are each chosen from hydrogen, divalent groups of formula (a), and divalent groups of formula (a'):

$$-\left[CH_2-CH\underset{R_1}{|}\right]_q-(V)_p-\qquad(a)$$

$$-CH=C\underset{R_1}{|}-(V)_p-\qquad(a')$$

wherein:
groups V, which are identical or different, are each chosen from —CH$_2$— groups and —CH$_2$—CH(OH)CH$_2$— groups;
groups $R_1$, which are identical or different, are each chosen from hydrogen and methyl groups; and
p is 0 or 1;
q is 0 or 1, with the proviso that p+q is different from 0; wherein said divalent groups of formula (a) and divalent groups of formula (a') allow the attachment of the radical A onto the silicon-containing chain; and
provided that at least one of $L_1$, $L_2$, $L_3$, and $L_4$ is chosen from said divalent groups of formula (a) and divalent groups of formula (a');
groups B are methyl groups;
r ranges from 0 to 5;
s ranges from 1 to 2;
u ranges from 1 to 6;
t ranges from 0 to 5;
with the proviso that t+u ranges from 3 to 6.

20. A compound according to claim 1, wherein said divalent groups of formula (a) and said divalent groups of formula (a') are chosen from optionally hydroxylated, linear and branched, saturated and unsaturated, divalent ($C_1$-$C_6$) alkyl groups.

21. A compound according to claim 20, wherein said divalent groups of formula (a) and said divalent groups of formula (a') are chosen from methylene (—CH$_2$—) groups, ethylene (—CH$_2$—CH$_2$—) groups, propylene (—CH$_2$—CH$_2$—CH$_2$—) groups,
n-butylene (—CH$_2$—CH$_2$—CH$_2$—CH$_2$—) groups, isobutylene (—CH$_2$—CH(CH$_3$)—CH$_2$—) groups, —CH=CH—CH$_2$— groups, —CH=C(CH$_3$)—CH$_2$— groups, —CH=CH—CH(CH$_3$)— groups, and CH$_2$—CH(OH)—CH$_2$— groups.

22. A compound according to claim 1, wherein said compound is chosen from:

5-(1,2-dihydroxyethyl)-3-hydroxy-4-(3-[1,3,3,3-tetramethyl-1-[(trimethylsilyl)oxy]disiloxanyl]propyloxy)-5H-furan-2-one;

5-(1,2-dihydroxyethyl)-4-hydroxy-3-(3-[1,3,3,3-tetramethyl-1-[(trimethylsilyl)oxy]disiloxanyl]propyloxy)-5H-furan-2-one;

5-(1,2-dihydroxyethyl)-3-hydroxy-4-[2-methyl-3-[1,3,3,3-tetramethyl-1-[(trimethylsilyl)oxy]disiloxanyl]propyloxy]-5H-furan-2-one;

5-(1,2-dihydroxyethyl)-4-hydroxy-3-[2-methyl-3-[1,3,3,3-tetramethyl-1-[(trimethylsilyl)oxy]disiloxanyl]propyloxy]-5H-furan-2-one;

5-(1,2-dihydroxyethyl)-4-[3-[3-[2-methyl-3-[1,3,3,3-tetramethyl-1-[(trimethylsilyl)oxy]disiloxanyl]propyloxy]-2-hydroxy-propyloxy]-3-hydroxy-5H-furan-2-one;

5-(1,2-dihydroxyethyl)-3-[3-[3-[2-methyl-3-[1,3,3,3-tetramethyl-1-[(trimethylsilyl)oxy]disiloxanyl]propyloxy]-2-hydroxy-propyloxy]4-hydroxy-5H-furan-2-one;

5-(1,2-dihydroxyethyl)-3-hydroxy-4-trimethylsilanylmethoxy-5H-furan-2-one;

5-(1,2-dihydroxyethyl)-4-hydroxy-3-(3-trimethylsilanylmethoxy)-5H-furan-2-one;

5-(1,2-dihydroxyethyl)-3-hydroxy-4-(3-trimethylsilanylpropyloxy)-5H-furan-2-one; and 5-(1,2-dihydroxyethyl)-4-hydroxy-3-(3-trimethylsilanylpropyloxy)-5H-furan-2-one.

23. A method for preparing the compound of claim 19 comprising:
A) grafting a corresponding Si—H containing derivative onto an organic derivative of ascorbic acid via hydrosilylation to form a product;
wherein:
1) the corresponding Si—H containing derivative is chosen from compounds of formula (5), formula (6) and formula (7):

H—SiR'$_1$R'$_2$R'$_3$ (5)

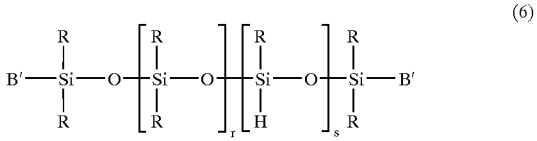

(6)

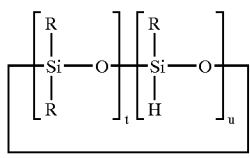

(7)

wherein:
groups R, which are identical or different, are chosen from trimethylsilyloxy groups of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated;

R'$_1$, R'$_2$, and R'$_3$, which are identical or different, are each chosen from linear and branched (C$_1$–C$_8$) alkyl groups, linear and branched (C$_1$–C$_8$) alkenyl groups, and trimethylsilyloxy groups of formula —O—SiMe$_3$;

r ranges from 0 to 50;
s ranges 0 from 20;
u ranges from 1 to 6;
t ranges from 0 to 9;
with the proviso that t+u ranges from 3 to 10;
groups B', which are identical or different, are chosen from groups R and hydrogen atoms, provided that if s=0, then at least one of the two groups B' is a hydrogen group; and 2) the organic derivative of ascorbic acid is chosen from the compounds of formula (I'):

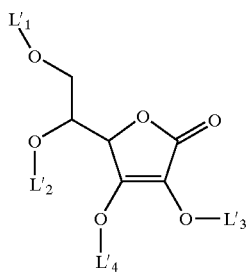

(I')

wherein:
L'$_1$, L'$_2$, L'$_3$, and L'$_4$, are chosen from benzyloxy groups, groups of formula (b), and groups of formula (b'):

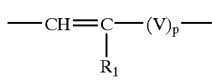

(b)

(b')

wherein:
the groups V, which are identical or different, are each chosen from linear and branched, saturated and unsaturated, divalent (C$_1$–C$_6$) alkyl groups, wherein said divalent (C$_1$–C$_6$) alkyl groups are optionally substituted with at least one group chosen from linear and branched, saturated and unsaturated (C$_2$–C$_8$) alkoxy groups and hydroxyl groups;

the groups R$_1$, which are identical or different, are each chosen from hydrogen, hydroxyl groups, and linear and branched, saturated and unsaturated (C$_1$–C$_8$) alkyl groups; and p is 0 or 1; and further wherein L'$_1$ and L'$_2$ may optionally form, together with the organic derivative of ascorbic acid, a methylenedioxy ring substituted with at least one group chosen from (C$_1$–C$_6$) alkyl groups and phenyl groups;

provided that at least one of L'$_1$, L'$_2$, L'$_3$, and L'$_4$ is chosen from the groups of formula (b) and the groups of formula (b'); and B) subsequently deprotecting the product.

24. A method for preparing the compound of claim 19, wherein the methylenedioxy ring is substituted with at least one group chosen from methyl groups, ethyl groups, and phenyl groups.

25. A method for preparing the compound of claim 19, wherein the product is deprotected by a process chosen from acid hydrolysis of the isopropylidenes, and debenzylation by catalytic hydrogenation.

26. A method for preparing the compound of claim 19, wherein the hydrosilylation is carried out in the presence of an effective amount of a platinum catalyst.

27. A method for preparing the silanes of formula (2) according to claim 1, comprising:
A) grafting a corresponding Si—H containing derivative onto an organic derivative of ascorbic acid via hydrosilylation to form a product:

wherein:
1) the corresponding Si—H containing derivative is chosen from compounds of formula (5), formula (6) and formula (7):

H—SiR'$_1$R'$_2$R'$_3$ (5)

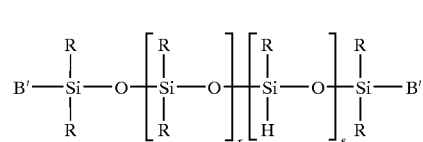

(6)

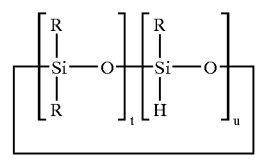

(7)

wherein:
groups R, which are identical or different, are chosen from trimethylsilyloxy groups of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated;

R'$_1$, R'$_2$, and R'$_3$, which are identical or different, are each chosen from linear and branched (C$_1$–C$_8$) alkyl groups, linear and branched (C$_1$–C$_8$) alkenyl groups, and trimethylsilyloxy groups of formula —O—SiMe$_3$;

r ranges from 0 to 50;
s ranges from 0 to 20;
u ranges from 1 to 6;
t ranges from 0 to 9;
with the proviso that t+u ranges from 3 to 10;
groups B', which are identical or different, are chosen from the radicals R and hydrogen, provided that if s=0, then at least one of the two radicals B' is hydrogen; and
2) the organic derivative of ascorbic acid is chosen from the compounds of the formula (I'):

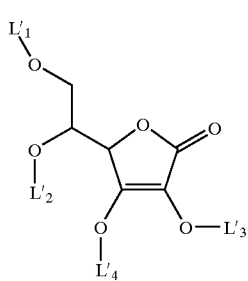

(I')

wherein:
$L'_1$, $L'_2$, $L'_3$, and $L'_4$ are chosen from benzyloxy groups, groups of formula (b), and groups of formula (b'):

wherein:
groups V, which are identical or different, are each chosen from —$CH_2$— groups and —$CH_2$—CH(OH)$CH_2$— groups;
$R_1$ is chosen from hydrogen and methyl groups; and
p is 1; and
further wherein $L'_1$ and $L'_2$ may optionally form, together with the organic derivative of ascorbic acid, a methylenedioxy ring substituted with at least one group chosen from ($C_1$–$C_6$) alkyl groups and phenyl groups;
provided that at least one of $L'_1$, $L'_2$, $L'_3$, and $L'_4$ is chosen from the groups of formula (b) and the groups of formula (b'); and
B) subsequently deprotecting the product.

28. A method for preparing the silanes of formula (2) according to claim 27, wherein the methylenedioxy ring is substituted with at least one group chosen from methyl groups, ethyl groups, and phenyl groups.

29. A method for preparing the silanes of formula (2), wherein the product is deprotected by a process chosen from acid hydrolysis of the isopropylidenes, and debenzylation by catalytic hydrogenation.

30. A method for preparing the silanes of formula (2), wherein the hydrosilylation is carried out in the presence of an effective amount of a platinum catalyst.

31. A method for preparing the silanes of formula (2) according to claim 1, comprising:
reacting a derivative of formula (I'''), defined below, with a silane derivative of formula (8), defined below, to form a product;

wherein:
a) the derivative of formula (I''') is:

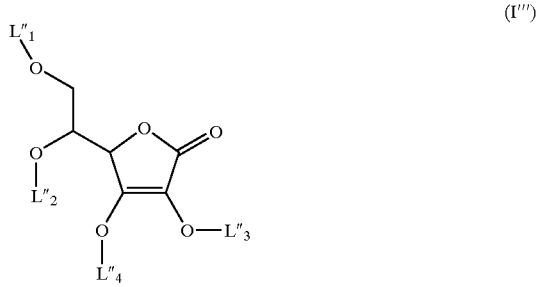

(I''')

wherein:
$L''_1$, $L''_2$, $L''_3$, and $L''_4$, which are identical or different, are each chosen from benzyloxy groups and hydrogen;
further wherein $L''_1$ and $L''_2$ may optionally form, together with the organic derivative of ascorbic acid, a methylenedioxy ring substituted with at least one group chosen from ($C_1$–$C_6$) alkyl groups and phenyl groups;
provided that at least one of $L''_1$, $L''_2$, $L''_3$, and $L''_4$ is hydrogen; and
b) the silane derivative of formula (8) is:

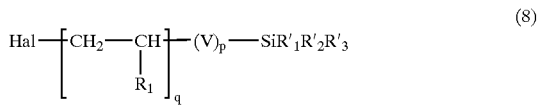

(8)

wherein:
Hal is a halogen atom;
$R_1$, is chosen from hydrogen, a hydroxyl group, and linear and branched, saturated and unsaturated ($C_1$–$C_8$) alkyl groups;
$R'_1$, $R'_2$, and $R'_3$, which are identical or different, are each chosen from linear and branched ($C_1$–$C_8$) alkyl groups, linear and branched ($C_1$–$C_8$) alkenyl groups, and trimethylsilyloxy groups of formula —O—$SiMe_3$;
V is chosen from linear and branched, saturated and unsaturated, divalent ($C_1$–$C_6$) alkyl groups, wherein said divalent ($C_1$–$C_6$) alkyl groups are optionally substituted with at least one group chosen from linear and branched, saturated and unsaturated, ($C_2$–$C_8$) alkoxy groups and a hydroxyl group; and
p is 0 or 1, q is 0 or 1, with the proviso that p+q is different from 0.

32. A method for preparing the silanes of formula (2), wherein Hal is chosen from chlorine and iodine.

33. A composition comprising a cosmetically or pharmaceutically acceptable medium and at least one silicon-containing compound derived from ascorbic acid having at least one group chosen from:
a) silicone-containing chains having at least one group of formula (1):

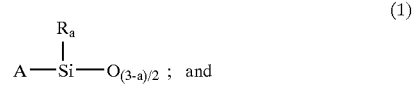

(1)

and b) silanes of formula (2):

$$A-SiR'_1R'_2R'_3 \quad (2)$$

wherein:
R is chosen from a trimethylsilyloxy group of formula $-O-SiMe_3$, and linear, cyclic and branched, saturated and unsaturated, $(C_1-C_{30})$ alkyl groups, wherein the $(C_1-C_{30})$ alkyl groups are optionally partially halogenated or optionally completely halogenated;
a is equal to 1 or 2,
$R'_1$, $R'_2$, and $R'_3$, which are identical or different, are each chosen from linear and branched $(C_1-C_8)$ alkyl groups, linear and branched $(C_1-C_8)$ alkenyl groups, and trimethylsilyloxy groups of formula $-O-SiMe_3$;
A is chosen from groups of formula (I):

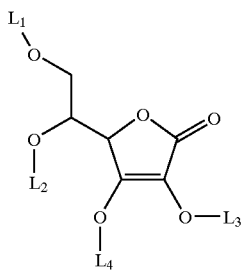

(I)

wherein:
$L_1$, $L_2$, $L_3$, and $L_4$, which are identical or different, are each chosen from hydrogen, divalent groups of formula (a), and divalent groups of formula (a'):

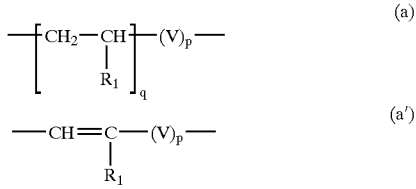

wherein:
groups V are identical or different, are each chosen from linear and branched, saturated and unsaturated, divalent $(C_1-C_6)$ alkyl groups, wherein said divalent $(C_1-C_6)$ alkyl groups are optionally substituted with at least one group chosen from linear and branched, saturated and unsaturated $(C_2-C_8)$ alkoxy groups and hydroxyl groups;
groups $R_1$, which are identical or different, are each chosen from hydrogen, hydroxyl groups, and linear and branched, saturated and unsaturated $(C_1-C_8)$ alkyl groups; and
units p, which are identical or different, are each chosen from 0 and 1;
q is 0 or 1, with the proviso that p+q is different from 0;
wherein said divalent groups of formula (a) and divalent groups of formula (a') allow the attachment of the radical A onto the silicon-containing chains; and
provided that at least one of $L_1$, $L_2$, $L_3$, and $L_4$ is chosen from said divalent groups of formula (a) and divalent groups of formula (a').

34. A composition according to claim 33, wherein said composition is a cosmetic composition.

35. A composition according to claim 33, wherein said composition is a pharmaceutical composition.

36. A composition according to claim 33, wherein said at least one silicone-containing compound is present in an amount ranging from about 0.1% to about 10% by weight, relative to the total weight of the composition.

37. A composition according to claim 36, wherein said at least one silicone-containing compound is present in an amount ranging from about 0.5% to about 5% by weight, relative to the total weight of the composition.

38. A composition according to claim 33, wherein said composition is suitable for application to a keratinous material.

39. A composition according to claim 38, wherein said keratinous material is chosen from body skin, facial skin, hair, eyelashes, eyebrows, mucous membranes, semi-mucous membranes, scalp, and nails.

40. A composition according to claim 33, wherein said composition is in any cosmetically or pharmaceutically acceptable form.

41. A composition according to claim 33, further comprising at least one adjuvant chosen from fatty substances, organic solvents, water, silicones, thickeners, emollients, sunscreens, antifoams, moisturizing agents, perfumes, preservatives, surfactants, fillers, sequestrants, anionic polymers, cationic polymers, nonionic polymers, amphoteric polymers, propellants, alkalinizing agents, acidifying agents, colorants, pigments, nanopigments, and cosmetic active agents.

42. A composition according to claim 41, wherein the fatty substances are chosen from oils, waxes, $(C_8-C_{32})$ fatty acids, $(C_8-C_{32})$ fatty acid esters, and $(C_8-C_{32})$ fatty alcohols.

43. A composition according to claim 42, wherein the fatty substances are chosen from petroleum jelly, paraffin, lanolin, hydrogenated lanolin, acetylated lanolin, hydrogenated palm oil, hydrogenated castor oil, liquid paraffin, paraffin oil, Purcellin oil, volatile silicone oils, non-volatile silicone oils, and isoparaffins.

44. A composition according to claim 41, wherein the organic solvents are chosen from $(C_1-C_6)$ lower polyols.

45. A composition according to claim 41, wherein the organic solvents are chosen from ethanol, isopropanol, propylene glycol, glycerin and sorbitol.

46. A composition according to claim 40, wherein the cosmetically or pharmaceutically acceptable form of the composition is a form suitable for at least one of: protection of human hair against UV radiation (anti-sun compositions); protection of human epidermis against UV radiation (anti-sun compositions); protection, treatment, and care of hair; body skin care; face care; and makeup for a body part chosen from eyelashes, eyebrows, hair, skin, and face.

47. A composition according to claim 40, wherein the cosmetically or pharmaceutically acceptable form of the composition is chosen from shampoos, lotions, gels, rinse-off compositions, foundations, lipsticks, eyeshadows, blushers, eyeliners, mascaras, dyeing gels, nail varnishes, and creams.

48. A composition according to claim 47, wherein the creams are chosen from epidermis creams, day creams, night creams, anti-wrinkle creams, moisturizing creams, foot creams and hand creams.

49. A method for treating oxidative stress and/or treating the effects of exposure to sunlight and/or preventing the ageing of a keratinous material comprising:

applying to a keratinous material an effective amount of at least one silicon-containing compound derived from ascorbic acid having at least one group chosen from:

a) silicone-containing chains having at least one group of formula (1):

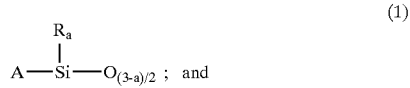  (1)

and b) silanes of formula (2):

  (2)

wherein:
R is chosen from a trimethylsilyloxy group of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated;
a is equal to 1 or 2,
R'$_1$, R'$_2$, and R'$_3$, which are identical or different, are each chosen from linear and branched (C$_1$–C$_8$) alkyl groups, linear and branched (C$_1$–C$_8$) alkenyl groups, and trimethylsilyloxy groups of formula —O—SiMe$_3$;
A is chosen from groups of formula (I):

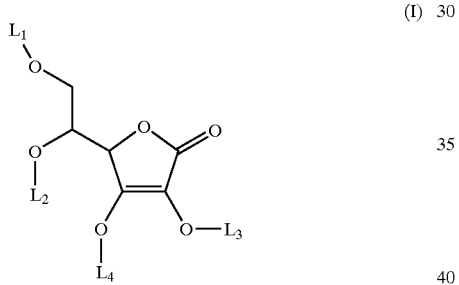  (I)

wherein:
L$_1$, L$_2$, L$_3$, and L$_4$, which are identical or different, are each chosen from hydrogen, divalent groups of formula (a), and divalent groups of formula (a'):

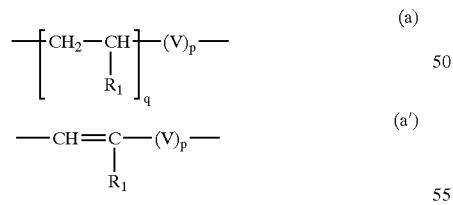

wherein:
groups V, which are identical or different, are each chosen from linear and branched, saturated and unsaturated, divalent (C$_1$–C$_6$) alkyl groups, wherein said divalent (C$_1$–C$_6$) alkyl groups are optionally substituted with at least one group chosen from linear and branched, saturated and unsaturated (C$_2$–C$_8$) alkoxy groups and hydroxyl groups;
groups R$_1$, which are identical or different, are each chosen from hydrogen, hydroxyl groups, and linear and branched, saturated and unsaturated (C$_1$–C$_8$) alkyl groups; and
units p, which are identical or different, are each chosen from 0 and 1;
q is 0 or 1, with the proviso that p+q is different from 0;
wherein said divalent groups of formula (a) and divalent groups of formula (a') allow the attachment of the radical A onto the silicon-containing chains; and
provided that at least one of L$_1$, L$_2$, L$_3$, and L$_4$ is chosen from said divalent groups of formula (a) and divalent groups of formula (a').

50. A method according to claim 49, wherein the keratinous material is chosen from skin, hair, eyelashes, eyebrows, and nails.

51. A method for treating oxidative stress and/or treating the effects of exposure to sunlight and/or preventing the ageing of a keratinous material comprising:
applying to keratinous material, an effective amount of a composition, comprising a cosmetically or pharmaceutically acceptable medium and at least one silicon-containing compound derived from ascorbic acid having at least one group chosen from:

a) silicone-containing chains having at least one group of formula (1):

  (1)

or b) silanes of formula (2):

  (2)

wherein:
R is chosen from a trimethylsilyloxy group of formula —O—SiMe$_3$, and linear, cyclic and branched, saturated and unsaturated, (C$_1$–C$_{30}$) alkyl groups, wherein the (C$_1$–C$_{30}$) alkyl groups are optionally partially halogenated or optionally completely halogenated;
a is equal to 1 or 2,
R'$_1$, R'$_2$, and R'$_3$, which are identical or different, are each chosen from linear and branched (C$_1$–C$_8$) alkyl groups, linear and branched (C$_1$–C$_8$) alkenyl groups, and trimethylsilyloxy groups of formula —O—SiMe$_3$;
A is chosen from groups of formula (I):

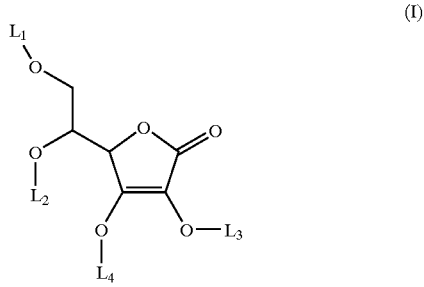  (I)

wherein:
L$_1$, L$_2$, L$_3$, and L$_4$, which are identical or different, are each chosen from hydrogen, divalent groups of formula (a), and divalent groups of formula (a'):

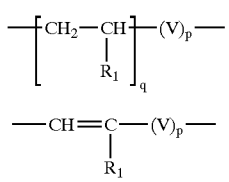

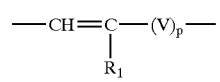

wherein:
- groups V, which are identical or different, are each chosen from linear and branched, saturated and unsaturated, divalent ($C_1$–$C_6$) alkyl groups, wherein said divalent ($C_1$–$C_6$) alkyl groups are optionally substituted with at least one group chosen from linear and branched, saturated and unsaturated ($C_2$–$C_8$) alkoxy groups and hydroxyl groups;
- groups $R_1$, which are identical or different, are each chosen from hydrogen, hydroxyl groups, and linear and branched, saturated and unsaturated ($C_1$–$C_8$) alkyl groups; and
- p is 0 or 1;
- q is 0 or 1, with the proviso that p+q is different from 0;
- wherein said divalent groups of formula (a) and divalent groups of formula (a') allow the attachment of the radical A onto the silicon-containing chains; and
- provided that at least one of $L_1$, $L_2$, $L_3$, and $L_4$ is chosen from said divalent groups of formula (a) and divalent groups of formula (a').

52. A method according to claim 51, wherein the keratinous material is chosen from skin, hair, eyelashes, eyebrows, and nails.

53. A method for treating oxidative stress and/or treating the effects of exposure to ionizing or solar radiation, and/or treating the effects of use of free radical generating medicaments, and/or preventing ageing of a keratinous material, comprising:
applying to a keratinous material an effective amount of a pharmaceutical composition comprising at least one silicon-containing compound derived from ascorbic acid having at least one group chosen from:
a) silicone-containing chains having at least one group of formula (1):

or b) silanes of formula (2):

wherein:
- R is chosen from a trimethylsilyloxy group of formula —O—SiMe$_3$, and linear, cyclic and branched, saturated and unsaturated, ($C_1$–$C_{30}$) alkyl groups, wherein the ($C_1$–$C_{30}$) alkyl groups are optionally partially halogenated or optionally completely halogenated;
- a is equal to 1 or 2,
- $R'_1$, $R'_2$, and $R'_3$, which are identical or different, are each chosen from linear and branched ($C_1$–$C_8$) alkyl groups, linear and branched ($C_1$–$C_8$) alkenyl groups, and trimethylsilyloxy groups of formula —O—SiMe$_3$;
- A is chosen from groups of formula (I):

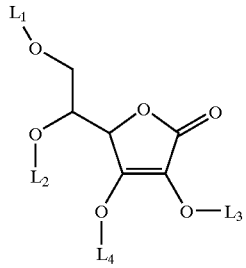

wherein:
- $L_1$, $L_2$, $L_3$, and $L_4$, which are identical or different, are each chosen from hydrogen, divalent groups of formula (a), and divalent groups of formula (a'):

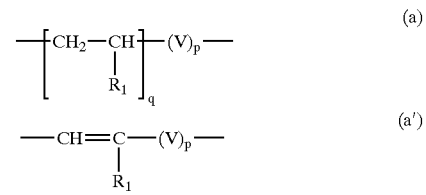

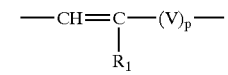

wherein:
- groups V, which are identical or different, are each chosen from linear and branched, saturated and unsaturated, divalent ($C_1$–$C_6$) alkyl groups, wherein said divalent ($C_1$–$C_6$) alkyl groups are optionally substituted with at least one group chosen from linear and branched, saturated and unsaturated ($C_2$–$C_8$) alkoxy groups and hydroxyl groups;
- groups $R_1$, which are identical or different, are each chosen from hydrogen, hydroxyl groups, and linear and branched, saturated and unsaturated ($C_1$–$C_8$) alkyl groups; and
- p, which are identical or different, are each chosen from 0 and 1;
- q is 0 or 1, with the proviso that p+q is different from 0;
- wherein said divalent groups of formula (a) and divalent groups of formula (a') allow the attachment of the radical A onto the silicon-containing chains; and
- provided that at least one of $L_1$, $L_2$, $L_3$, and $L_4$ is chosen from said divalent groups of formula (a) and divalent groups of formula (a').

54. A method according to claim 53, wherein the keratinous material is chosen from skin, hair, eyelashes, eyebrows, and nails.

* * * * *